(12) United States Patent
Kim et al.

(10) Patent No.: US 11,931,000 B2
(45) Date of Patent: Mar. 19, 2024

(54) OPENABLE SPINAL ENDOSCOPE APPARATUS

(71) Applicants: THE CATHOLIC UNIVERSITY OF KOREA INDUSTRY-ACADEMIC COOPERATION FOUNDATION, Seoul (KR); S-MEDION CO., LTD., Seoul (KR)

(72) Inventors: Jin Sung Kim, Yongin-si (KR); Ji Woon Chun, Seoul (KR); Hyang Mi Oh, Seoul (KR)

(73) Assignees: THE CATHOLIC UNIVERSITY OF KOREA INDUSTRY-ACADEMIC COOPERATION FOUNDATION, Seoul (KR); S-MEDION CO., LTD., Seoul (KR)

( * ) Notice: Subject to any disclaimer, the term of this patent is extended or adjusted under 35 U.S.C. 154(b) by 333 days.

(21) Appl. No.: 16/982,308

(22) PCT Filed: Oct. 10, 2018

(86) PCT No.: PCT/KR2018/011854
§ 371 (c)(1),
(2) Date: Sep. 18, 2020

(87) PCT Pub. No.: WO2019/182215
PCT Pub. Date: Sep. 26, 2019

(65) Prior Publication Data
US 2021/0007587 A1    Jan. 14, 2021

(30) Foreign Application Priority Data
Mar. 20, 2018  (KR) .................. 10-2018-0031878

(51) Int. Cl.
*A61B 1/00* (2006.01)
*A61B 1/018* (2006.01)
(Continued)

(52) U.S. Cl.
CPC ...... *A61B 1/00105* (2013.01); *A61B 1/00066* (2013.01); *A61B 1/00073* (2013.01);
(Continued)

(58) Field of Classification Search
CPC . A61B 1/018; A61B 1/00066; A61B 1/00073; A61B 1/00135; A61B 1/04;
(Continued)

(56) References Cited

U.S. PATENT DOCUMENTS 5,213,093 A * 5/1993 Swindle ................ A61B 1/018
                                                         600/920
5,349,941 A * 9/1994 Hori ................... A61B 1/00135
                                                         600/122
(Continued)

FOREIGN PATENT DOCUMENTS

CN      104107073 A     10/2014
EP       2596738 B1      9/2014
(Continued)

*Primary Examiner* — Timothy J Neal
*Assistant Examiner* — James Edward Boice
(74) *Attorney, Agent, or Firm* — Bridgeway IP Law Group, PLLC; Sang Ho Lee; Hyun Woo Shin

(57) ABSTRACT

The present disclosure relates to an openable/closable vertebral endoscopic device. The openable/closable vertebral endoscopic device includes an endoscope body including a working channel for providing an access route of a surgical instrument to a diseased area of a human body, the working channel having an open channel formed by opening a portion of the working channel such that a portion of the surgical instrument inserted into the working channel is exposed to the outside; and a cover member provided on the endoscope body to selectively open or close the open channel of the endoscope body.

13 Claims, 6 Drawing Sheets

(51) Int. Cl.
*A61B 1/04* (2006.01)
*A61B 1/317* (2006.01)

(52) U.S. Cl.
CPC .......... *A61B 1/00135* (2013.01); *A61B 1/018* (2013.01); *A61B 1/04* (2013.01); *A61B 1/317* (2013.01)

(58) Field of Classification Search
CPC ............ A61B 1/00071; A61B 1/00105; A61B 1/00131; A61B 1/3135; A61B 1/317; A61B 1/303; A61B 1/307; A61B 17/3415; A61B 1/00; A61B 1/313; A61B 1/00119; A61B 1/267; A61M 2039/0626
USPC ........................................................ 600/104
See application file for complete search history.

(56) References Cited

U.S. PATENT DOCUMENTS

| | | | | |
|---|---|---|---|---|
| 5,401,248 A | * | 3/1995 | Bencini | A61M 39/06 251/149.3 |
| 5,800,344 A | * | 9/1998 | Wood, Sr. | A61B 1/267 600/196 |
| 6,605,094 B1 | * | 8/2003 | Mann | A61B 17/3401 606/129 |
| 9,066,656 B2 | | 6/2015 | Irion et al. | |
| 10,398,543 B1 | * | 9/2019 | Solar | A61F 2/12 |
| 2004/0034369 A1 | * | 2/2004 | Sauer | A61B 1/012 606/139 |
| 2007/0088247 A1 | * | 4/2007 | Bliweis | A61B 17/3421 606/21 |
| 2012/0157772 A1 | * | 6/2012 | James | A61B 1/00135 600/156 |
| 2013/0267777 A1 | * | 10/2013 | Avitsian | A61B 1/00066 600/123 |
| 2016/0007982 A1 | * | 1/2016 | Liu | A61B 17/02 600/102 |
| 2018/0008309 A1 | * | 1/2018 | Kuwae | A61B 17/3421 |
| 2018/0303314 A1 | * | 10/2018 | Noyes | A61B 1/00124 |

FOREIGN PATENT DOCUMENTS

| | | |
|---|---|---|
| KR | 10-1737997 B1 | 5/2017 |
| WO | 2016-152626 A1 | 9/2016 |

* cited by examiner

OPENABLE SPINAL ENDOSCOPE APPARATUS

TECHNICAL FIELD

The present disclosure relates to openable/closable vertebral endoscopic devices, and more particularly, to an openable/closable vertebral endoscopic device having an improved structure such that precise and rapid treatment tailored to a patient is possible due to an increase in the space utilization of surgical instruments during spinal surgery using an endoscope, and the convenience of a surgical operator is increased.

BACKGROUND ART

In general, compared to open surgery, which opens a large incision in a major part of the body, surgery is performed by forming at least one incision within 0.5 to 2 cm in a specific part of the body and then inserting various surgical instruments including a video camera through the hole. This surgery is called a laparoscopic surgery. Because the laparoscopic surgery has a small incision size compared to traditional open surgery, the surgical wound looks more aesthetically pleasing, the pain from the wound is much less, and the hospital stay is short because the patient's recovery is quick due to the small wound. Also, a return to a daily life is quick.

Laparoscopic surgery is performed in most diseases of almost all departments except some cancers. Recently, surgery for the treatment of patients with spinal diseases has also been performed via the vertebral endoscopy of forming an incision within 5 to 20 mm in the back of a patient, inserting an endoscope through the incision, and then treat spinal diseases using the endoscope, instead of a typical operation of cutting the skin tissue of the patient's back and taking the spinal out to treat spinal diseases.

In spinal endoscopy treatment, a medical device for treatment such as an endoscope is inserted through an incision and pushed into the spine, and then a protruding disc piece is picked up with forceps or burned with a laser or high frequency to remove the cause of spinal disease.

Since most of these spinal endoscopy treatments do not require general anesthesia, side effects caused by anesthesia can be remarkably reduced, and occurrence of various side effects is greatly reduced due to rapid recovery because no wound remains large. Thus, the number of surgeries is increasing recently.

Conventional spinal endoscopy treatment has a limitation in expanding the outer diameter of the endoscope as much as the endoscope is inserted using a small incision, and the operation time of the conventional spinal endoscopy treatment is extended as the operation is performed in a limited space. Inside the endoscope (corresponding to a working channel part of the endoscope), a movement of other instruments and the size of the instruments were limited.

The background technology of the present disclosure is disclosed in Korean Patent Publication No. 10-1737997 (registered on May 15, 2017, Title of the invention: a cannula for percutaneous intervertebral foramen dilatation and an intervertebral cavity expansion device having the cannula).

DESCRIPTION OF EMBODIMENTS

Technical Problem

Provided is an openable/closable vertebral endoscopic device enabling smooth insertion of surgical instruments of various sizes into a working channel of an endoscopic device according to different required procedures for different diseased areas for different patients, and also enabling securement of angular flexibility during handling of the surgical instrument, thereby enhancing convenience and precision of a surgical operation.

Technical Solution

According to an aspect of the present disclosure, an openable/closable vertebral endoscopic device includes an endoscope body including a working channel for providing an access route of a surgical instrument to a diseased area of a human body, the working channel having an open channel formed by opening a portion of the working channel such that a portion of the surgical instrument inserted into the working channel is exposed to the outside; and a cover member provided on the endoscope body to selectively open or close the open channel of the endoscope body.

The cover member may have a shape of surrounding the working channel of the endoscope body, may include a closed portion closing the open channel and an open portion opening the open channel, the closed portion and the open portion being integrally formed with each other, and may be provided on the endoscope body to be rotatable relative to the endoscope body such that the closed portion and the open portion alternately close and open the open channel.

The cover member may have a shape of a cylinder having an empty inside to wrap the endoscope body, and include the open portion and the closed portion by cutting a circular arc portion corresponding to a certain angle in a circumferential direction.

The cover member may further include a level part radially protruding from the closed portion toward the outside of the closed portion and rotating together with the closed portion so that a surgical operator may smoothly open and close the open channel.

The endoscope body may include a working sleeve part extending in one axis direction and including the working channel having the open channel; a lens part provided on the working sleeve part so that the diseased area is photographed; and a manipulation part connected to the working sleeve part so that a surgical operator handles the working sleeve part at a location apart from the working sleeve part.

Advantageous Effects of Disclosure

An openable/closable vertebral endoscopic device having such a structure described above according to an embodiment of the present disclosure includes an open channel formed in an endoscope body to expand the space of the working channel for providing an access route of a surgical instrument to the diseased area of a human body, and opens or closes the open channel by using a cover member according to different treatments required for different patients, thereby enabling rapid and precise surgical operation tailored for a patient. In addition, the openable/closable vertebral endoscopic device may provide a quality medical service from a surgical operator, because angular flexibility of the surgical instrument inserted into the working channel is secured to some degree by the open channel.

BEST MODE

An openable/closable vertebral endoscopic device according to an embodiment of the present disclosure will now be described in detail with reference to the accompanying drawings.

Figure 1:
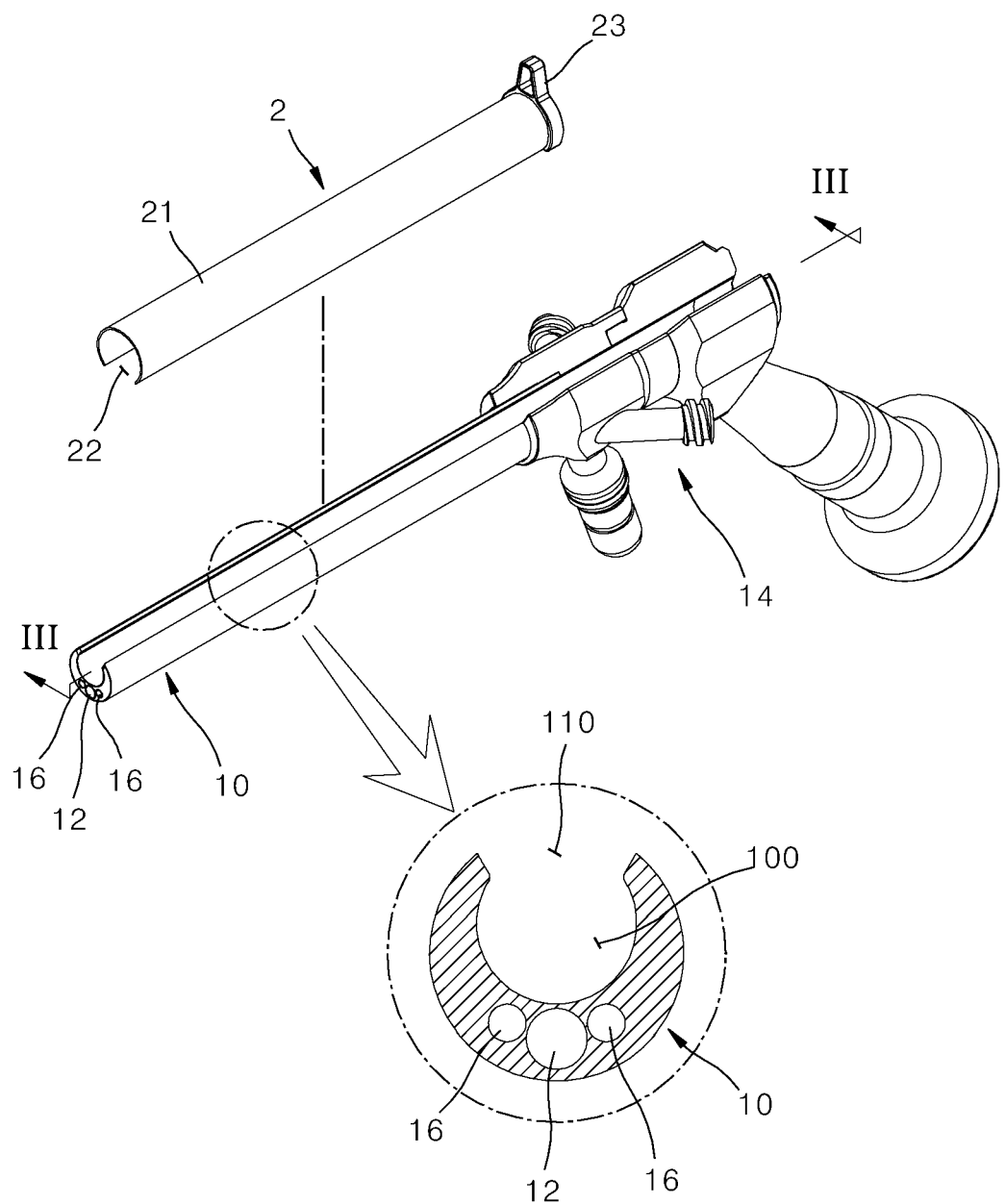
FIG. 1 is an exploded perspective view of an openable/closable vertebral endoscopic device according to an embodiment of the present disclosure.
Figure 2:
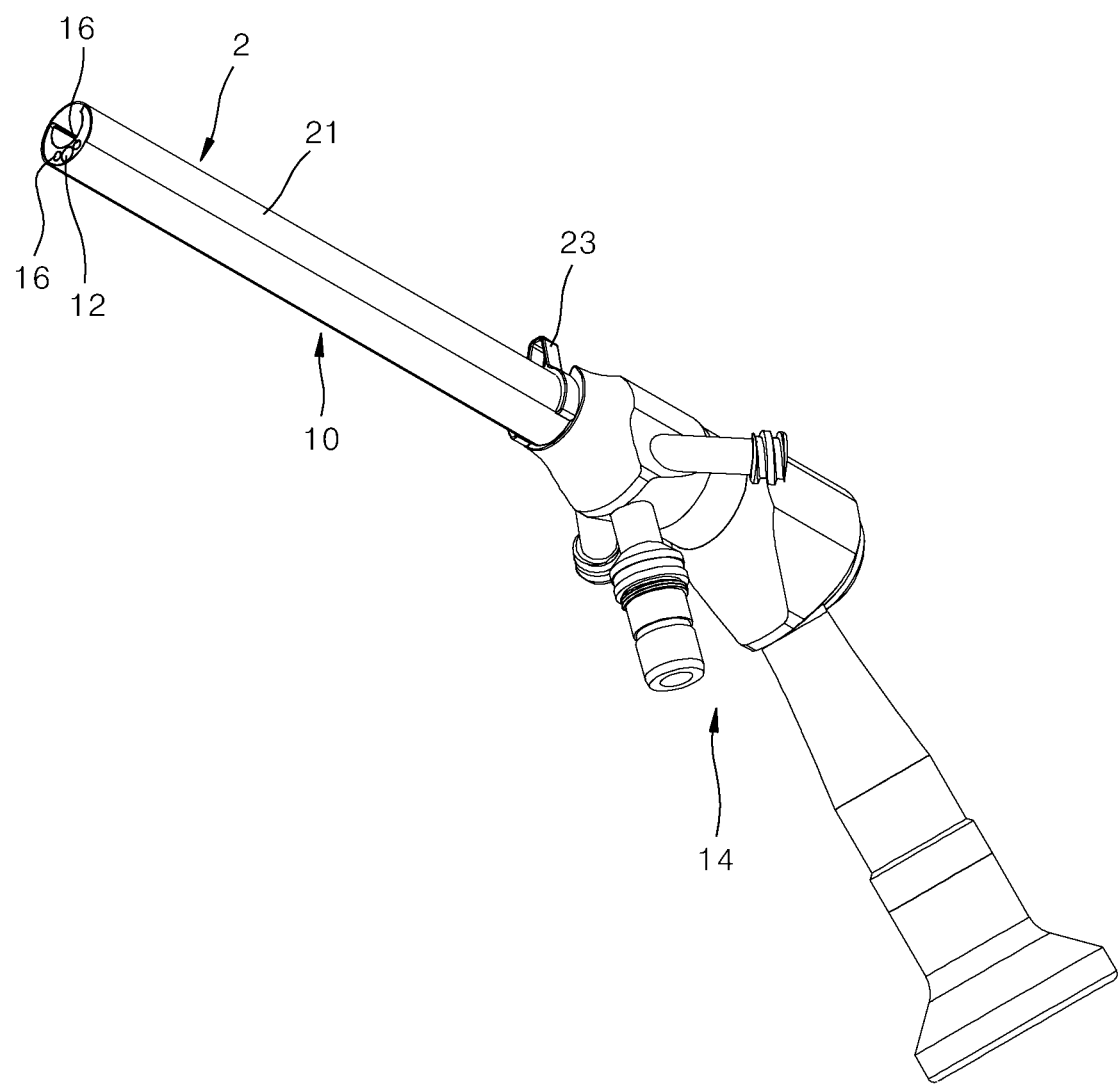
FIG. 2 is a bottom perspective view of a combined openable/closable vertebral endoscopic device according to an embodiment of the present disclosure.
Figure 3:
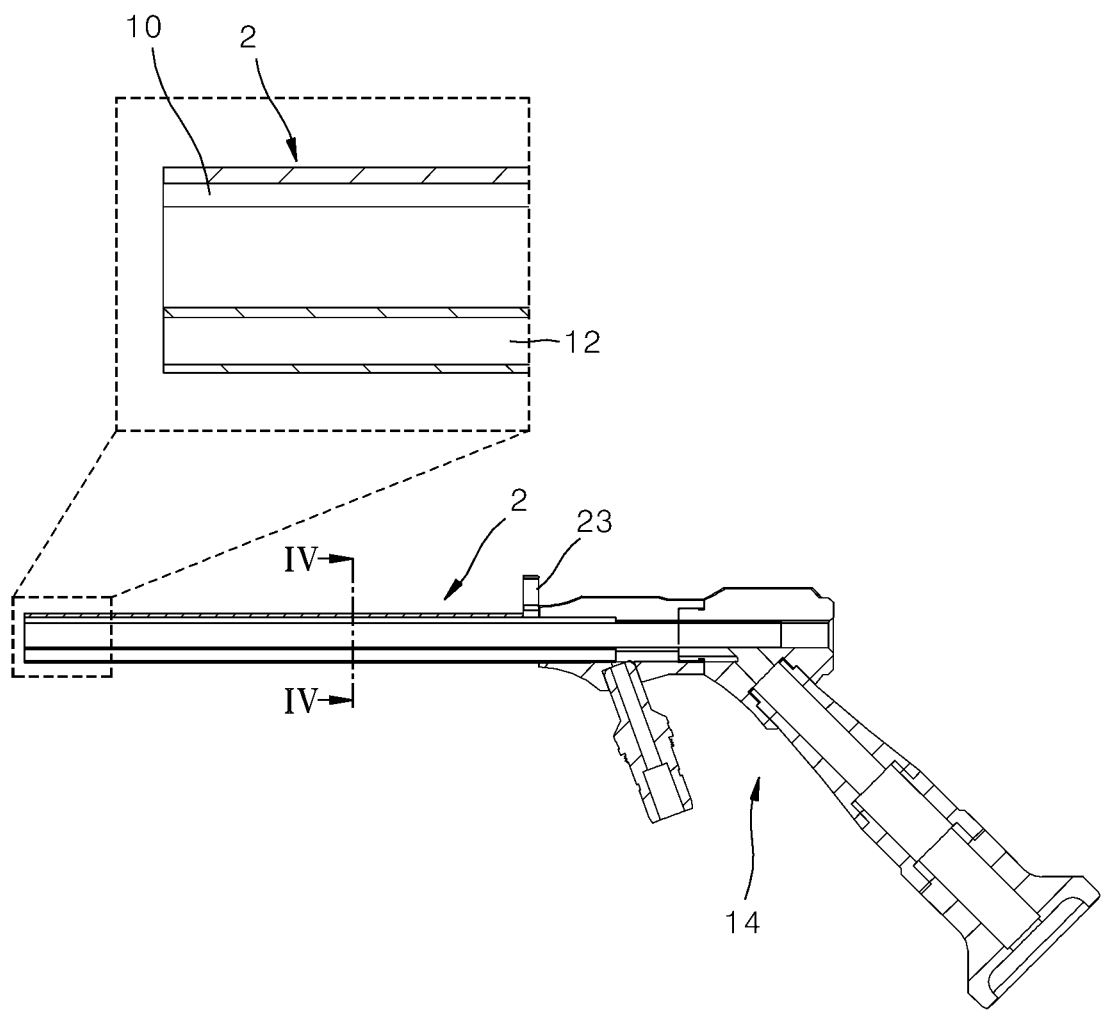
FIG. 3 is a cross-sectional view taken along line III-III of FIG. 1.
Figure 4:
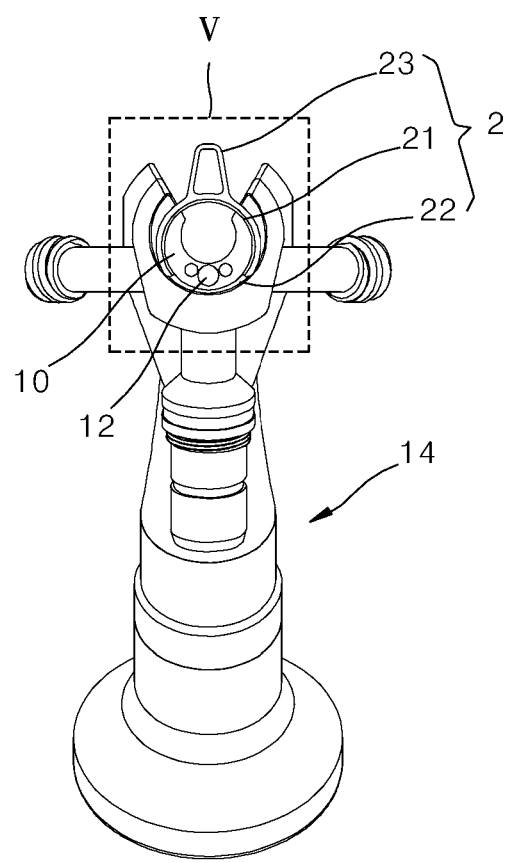
FIG. 4 is a cross-sectional view taken along line IV-IV of FIG. 3.
Figure 5:
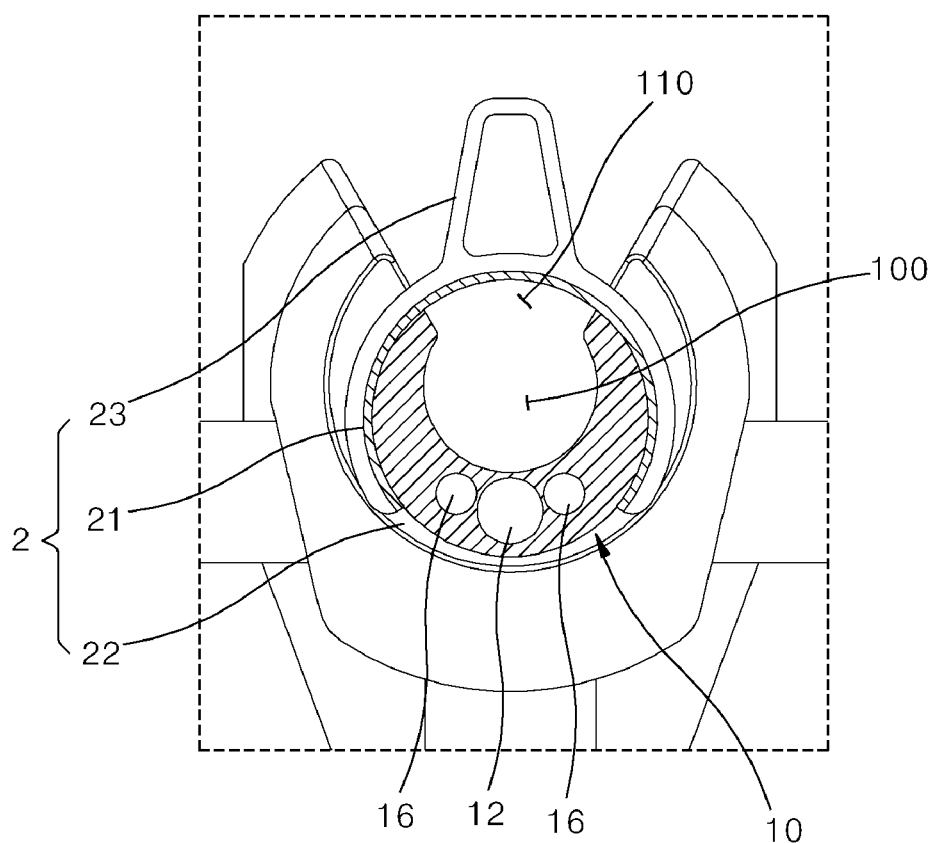
FIGS. 5 and 6 are views for explaining an operation of an embodiment of the present disclosure, by magnifying a portion V of FIG. 4.
Figure 6:
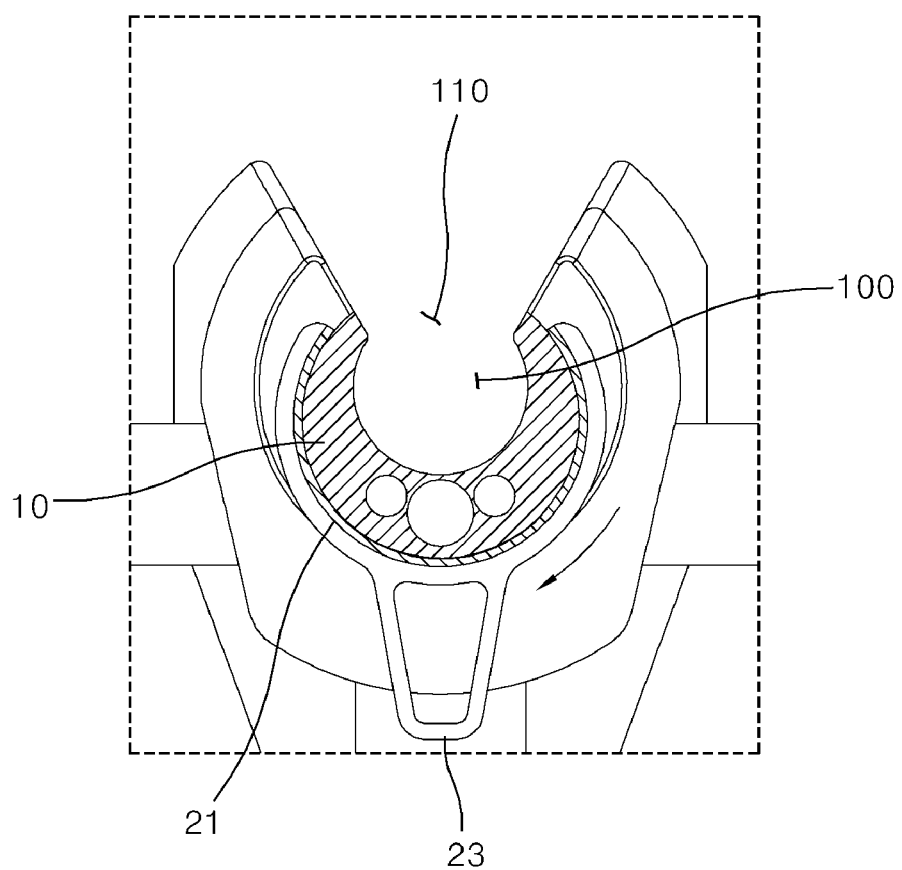

FIG. 1 is an exploded perspective view of an openable/closable vertebral endoscopic device according to an embodiment of the present disclosure, FIG. 2 is a bottom perspective view of a combined openable/closable vertebral endoscopic device according to an embodiment of the present disclosure, FIG. 3 is a cross-sectional view taken along line III-III of FIG. 1, FIG. 4 is a cross-sectional view taken along line IV-IV of FIG. 3, and FIGS. 5 and 6 are views for explaining an operation of an embodiment of the present disclosure, by magnifying a portion V of FIG. 4.

As shown in FIGS. 1 through 6, the openable/closable vertebral endoscopic device according to an embodiment of the present disclosure includes an endoscope body 1 and a cover member 2.

The endoscope body 1 has a similar structure to an endoscope for use in spine surgery, and obtains a unique effect unexpectable from general endoscopes due to an organic combination of a structure related to a working channel 100 according to the present embodiment with a general endoscope structure.

In other words, as shown in FIG. 1, the endoscope body 1 employed in the present embodiment includes the working channel 100 for providing an access route of a surgical instrument to a diseased area of a human body, wherein the working channel 100 includes an open channel 110 obtained by opening a portion of the working channel 100 such that a portion of the surgical instrument inserted into the human body is exposed to the outside.

A working channel employed in general endoscopes is formed as an enclosed type and thus it is difficult to expect insertion of a surgical instrument having a larger inner diameter than that of the working channel. However, according to the present embodiment, because the working channel 100 employed in the endoscope body 1 is provided with the open channel 110, surgical instruments of various sizes according to different treatments for different patents may access diseased areas through the working channel 100 having an expanded space due to formation of the open channel 110.

The cover member 2 is provided on the endoscope body 1 as shown in FIGS. 1 and 2, and selectively opens or closes the open channel 110 of the endoscope body 1 as shown in FIGS. 5 and 6.

In other words, in order for a surgical instrument according to a treatment required by a patient to be inserted into the working channel 100 of the endoscope body 1, the cover member 2 may close the open channel 110 as shown in FIG. 5 when use of a surgical instrument suitable for the original space of the working channel 100 is required, and may open the open channel 110 to secure an expanded space as shown in FIG. 6 when use of a surgical instrument having a larger size than the original space of the working channel 100 is required.

The openable/closable vertebral endoscopic device having this structure according to an embodiment of the present disclosure includes the open channel 110 formed in the endoscope body 1 to expand the space of the working channel 100 for providing an access route of the surgical instrument to the diseased area of the human body, and opens or closes the open channel 110 by using the cover member 2 according to different treatments required for different patients, thereby enabling rapid and precise surgical operation tailored for a patient. In addition, the openable/closable vertebral endoscopic device having this structure according to an embodiment of the present disclosure may provide a quality medical service from a surgical operator, because angular flexibility of the surgical instrument inserted into the working channel 100 is secured to some degree by the open channel 110.

The cover member 2 may have any of various structures capable of selectively open or close the open channel 110 of the endoscope body 1. However, according to the present embodiment, the cover member 2 is formed to wrap the working channel 100 of the endoscope body 1, as shown in FIG. 3, a closed portion 21 and an open portion 22 are integrally formed as shown in FIG. 4, and the cover member 2 is provided on the endoscope body 1 to be rotatable relative to the endoscope body 1 as shown in FIGS. 5 and 6.

In the present embodiment having this structure, because the cover member 2 rotates at a certain angle with respect to the endoscope body 1, the closed portion 21 and the open portion 22 alternately open or close the open channel 110, and thus the space of the working channel 100 of the endoscope body 1 may be freely expanded even with a simple manipulation by a surgical operator.

The open portion 22 and the closed portion 21 of the cover member 2 are formed by cutting out a circular arc portion corresponding to a certain angle in a circumferential direction, from a cylindrical structure having an empty inside to wrap the endoscope body 1 and extending in one direction.

Because the present embodiment having this structure includes the cover member 2 that has a simple structure and is easily formed, manufacturing costs of products may be reduced, and mass production thereof may be improved.

Because the cover member 2 includes a lever part 23 protruding from the closed portion 21 toward the outside of the closed portion 21 and rotating with the closed portion 21, a surgical operator may more smoothly open or close the open channel 110.

The endoscope body 1 may have any of various structures in which the open channel 110 is formed in the working channel 100. However, according to the present embodiment, the endoscope body 1 may include a working sleeve part 10, a lens part, and a manipulation part 14.

The working sleeve part 10 extends in one axis direction and includes the working channel 100 having the open channel 110, and the lens part is provided on the working sleeve part 10 to enable photographing of a diseased area, and includes not only a lens (not shown) mounted on a leading end of the working sleeve part 10 but also a channel 12 on the lens part's side that provides a moving path of light radiated onto the lens.

The manipulation part 14 is connected to the working sleeve part 10 and is provided with a structure such as a handle held by a surgical operator or a guide that guides insertion of a surgical instrument into the working sleeve part 10, and thus enables the surgical operator to handle the working sleeve part 10 at a location apart from the working sleeve part 10.

In the present embodiment having this structure, because a structure related to the working sleeve part 10 according to the present embodiment is organically combined with the structure of a general endoscope, a product enabling a rapid and precise surgical operation tailored to a patient may be manufactured due to a change in the structure of the working sleeve part 10 without a big change in a conventional endoscope structure, and thus may have an improved quality without causing an increase in the product's prices, thereby contributing to improving medical welfare.

Reference numeral 16 indicates a channel on a cleaning part's side that provides a spraying path for spraying a cleaning solution to a diseased area.

Although various embodiments of the present disclosure have been described above, the present embodiments and the drawings attached to the present specification merely show a part of the technical spirit included in the present disclosure. It will be apparent that modifications and specific embodiments that can be easily inferred by those skilled in the art within the scope of the technical idea are included in the scope of the present disclosure.

The invention claimed is:

1. A vertebral endoscopic device comprising:
    an endoscope body having;
        a working sleeve part, the working sleeve part having a working channel and an open channel, wherein the working channel and the open channel are through-holes elongated in a longitudinal direction of the endoscope body and are configured to accommodate a surgical instrument, and the open channel is defined by a circular arc opening corresponding to a predetermined angle with respect to a circumferential direction of the working channel, and
        a manipulation part having,
            a handle including,
                an elongated handheld structure having a through-hole therein, and
                a guide protruded in an opposite direction from the elongated handheld structure and connected to the working channel and the open channel,
            wherein the guide has a greater external dimension than the working sleeve part, the guide has a pair of incline planes expanding in parallel to imaginary lines, which define the open channel at the predetermined angle with respect to the circumferential direction of the working channel, and
            wherein the surgical instrument inserted into the working channel is exposed to outside through the open channel; and
        a cover having:
            a closed portion and an open portion, wherein the closed portion and the open portion have a structure surrounding the working sleeve part, and
            a lever disposed on an outer circumferential surface of the cover,
        wherein the cover is configured to rotate around the working sleeve part around a direction parallel to the longitudinal direction of the endoscope as an axis by rotating the lever to selectively open or close the open channel of the endoscope body.

2. The vertebral endoscopic device of claim 1, wherein the closed portion and the open portion are configured to alternately close and open the open channel as the cover rotates around the working sleeve part.

3. The vertebral endoscopic device of claim 2, wherein the closed portion of the cover has a greater circumferential length than the open portion of the cover.

4. The vertebral endoscopic device of claim 2, wherein the open portion of the cover has a greater circumferential length than a circumferential length of the open channel of the working channel.

5. The vertebral endoscopic device of claim 1, wherein the working sleeve part is elongated in the longitudinal direction thereof and comprises
    a lens channel, and
    at least one cleaning channel configured to spray a cleaning solution.

6. The vertebral endoscopic device of claim 5, wherein one of the at least one cleaning channel is located adjacent to the lens channel.

7. The vertebral endoscopic device of claim 5, wherein the working sleeve part is extended along the longitudinal direction of the endo scope body, and the working sleeve part has a structure having the open channel from one end to another end thereof.

8. The vertebral endoscopic device of claim 1, wherein a cross-section of the working channel and a cross-section view of the working sleeve part are eccentric circles.

9. The vertebral endoscopic device of claim 1, wherein the surgical instrument having an external dimension greater than an internal dimension of the working channel is accommodated in the working channel, the open channel, and the guide.

10. A vertebral endoscopic device comprising:
    an endoscope body having:
        a working sleeve part, the working sleeve part having
            a working channel, and
            an open channel,
            wherein the working channel and the open channel are through-holes elongated in a first direction and are configured to accommodate a surgical instrument, and the open channel is defined by a circular arc opening corresponding to a predetermined angle with respect to a circumferential direction of the working channel, and
            wherein the surgical instrument inserted into the working channel is exposed to outside through the open channel;
        a manipulation part having,
            a handle including,
                an elongated handheld structure having a through-hole therein, and
                a guide protruded in an opposite direction from the elongated handheld structure and connected to the working channel and the open channel,
            wherein the guide has a greater external dimension than the working sleeve part, the guide has a pair of incline planes expanding in parallel to imaginary lines, which define the open channel at the predetermined angle with respect to the circumferential direction of the working channel, and
        a cover having:
            a closed portion and an open portion, wherein the closed portion and the open portion have a structure surrounding the working sleeve part, and
            a lever disposed on an outer circumferential surface of the cover,
        wherein the cover is configured to rotate around the working sleeve part around a direction parallel to the first direction as an axis by rotating the lever to selectively open or close the open channel of the endoscope body, wherein the closed portion and the open portion are configured to alternately close and open the open channel as the cover rotates around the working channel, wherein the open portion of the cover is defined by a circular arc cover opening corresponding to the predetermined angle in a circumferential direction thereof, wherein the working sleeve part is extended in the first direction and comprises:
  a lens channel, and
  at least one cleaning channel configured to spray a cleaning solution,
and
wherein one of the at least one cleaning channel is located adjacent to the lens channel.

11. The vertebral endoscopic device of claim 10, wherein the working sleeve part is extended along the first direction and has one end and another end, and the working sleeve part has a structure maintaining the open channel having the circular arc opening corresponding to the predetermined angle with respect to the circumferential direction of the working channel from the one end to another end thereof.

12. The vertebral endoscopic device of claim 10, wherein the closed portion of the cover has a greater circumferential length than the open portion of the cover.

13. The vertebral endoscopic device of claim 10, wherein the open portion of the cover has a greater circumferential length than a circumferential length of the open channel of the working channel.

* * * * *